United States Patent [19]

Tang et al.

[11] Patent Number: 6,010,497

[45] Date of Patent: Jan. 4, 2000

[54] METHOD AND APPARATUS FOR CONTROLLING SCANNING OF AN ABLATING LASER BEAM

[75] Inventors: Fuqian Tang; Ming-Yi Hwang, both of Orlando, Fla.

[73] Assignee: LaserSight Technologies, Inc., Winter Park, Fla.

[21] Appl. No.: 09/001,398

[22] Filed: Jan. 7, 1998

(Under 37 CFR 1.47)

[51] Int. Cl.$^7$ .................................................. A61B 17/36
[52] U.S. Cl. .................................................. 606/5; 606/4
[58] Field of Search .............................. 606/4, 5, 6, 10, 606/11, 12

[56] References Cited

U.S. PATENT DOCUMENTS 3,697,889 10/1972 Dewey, Jr. .
3,743,965 7/1973 Offner .

(List continued on next page.)

FOREIGN PATENT DOCUMENTS

| 0 151869 a1 | 8/1985 | European Pat. Off. . |
| 0368512A2 | 5/1990 | European Pat. Off. . |
| 0418890A3 | 3/1991 | European Pat. Off. . |

OTHER PUBLICATIONS

D. Eimerl, L. Davis, & S. Vlesko, Optical, mechanical, and thermal properties of barium borate, Journal of Applied Physics, Sep. 1987, pp. 1968–1983.

J.T. Lin, Non–linear crystals for tunable coherent sources, Optical and Quatum Electronics, 1990, pp. S283–S313.

J.T. Lin, Temperature–tuned noncritically phase–matched frequency conversion in LiB3O5 crystal, Optics Communications, Dec. 1990, pp. 159–165.

Y. Tanaka, H. Kuroda, & S. Shionoya, Generation of Tunable Picsecond Pulses in the Ultraviolet Region Down to 197nm, May 1982, pp. 434–436.

Qiushi Ren, Raymond P. Galitis, Keith P. Thompson, & J.T. Lin, "Ablation of the Cornea and Synthetic Polymers using a UV (213 nm) Solid State Laser", IEE Journal of Quatum Electronics, Dec. 1990, pp. 2284–2288.

Conference on Lasers and Electro–Optics, Optical Society of America, May 1990, pp. 28–30.

G.P.A. Malcom, M.A. Persaud, & A.I. Ferguson, "Resonant Frequence Quadrupling of a Mode—Locked Diode—Pumped Nd: YLF Laser", Optics Letters, Jul. 1991, pp. 983–985.

(List continued on next page.)

*Primary Examiner*—Linda C. M. Dvorak
*Assistant Examiner*—Sonya Harris-Ogugua
*Attorney, Agent, or Firm*—William H. Bollman; Farkas & Manelli PLLC

[57] ABSTRACT

A laser beam delivery system and a method for ablating tissue, e.g., for reshaping a cornea of an eye is provided. The laser beam delivery system directs a laser beam on the tissue to be ablated in a predetermined pattern according to the principles of the present invention. The laser beam is incrementally scanned to subsequent laser beam ablation points or spots in the ablation zone in accordance with the predetermined pattern. The laser beam ablates tissue at the spots in the predetermined pattern in an arranged order. In one aspect of the present invention, the radii of the predetermined pattern is varied between scans of the laser beam until a predetermined reshaping is achieved by ablation. In another aspect of the present invention, every other, every third, every fourth, etc. laser beam spot in a predetermined pattern is ablated, and the scans are repeated for unablated points until all spots are ablated. In yet another aspect of the present invention, one or more layers in each of a plurality of annular ablation zones may be fully ablated before ablation in other annular ablation zones is performed.

34 Claims, 2 Drawing Sheets

U.S. PATENT DOCUMENTS

| | | |
|---|---|---|
| 3,848,104 | 11/1974 | Locke . |
| 3,938,058 | 2/1976 | Yamamoto . |
| 3,982,541 | 9/1976 | L'Esperance, Jr. . |
| 3,983,507 | 9/1976 | Tang et al. . |
| 4,180,751 | 12/1979 | Ammann . |
| 4,349,907 | 9/1982 | Campillo et al. . |
| 4,386,428 | 5/1983 | Baer . |
| 4,477,159 | 10/1984 | Mizuno et al. . |
| 4,520,816 | 6/1985 | Schachar et al. . |
| 4,538,608 | 9/1985 | L'Esperance, Jr. . |
| 4,573,467 | 3/1986 | Rich et al. . |
| 4,580,559 | 4/1986 | L'Esperance, Jr. . |
| 4,633,866 | 1/1987 | Peyman et al. . |
| 4,665,913 | 5/1987 | L'Esperance, Jr. ......................... 606/5 |
| 4,669,466 | 6/1987 | L'Esperance, Jr. . |
| 4,718,418 | 1/1988 | L'Esperance, Jr. ......................... 606/5 |
| 4,721,379 | 1/1988 | L'Esperance, Jr. . |
| 4,729,372 | 3/1988 | L'Esperance, Jr. . |
| 4,729,373 | 3/1988 | Peyman . |
| 4,732,148 | 3/1988 | L'Esperance, Jr. . |
| 4,733,660 | 3/1988 | Izkan ....................... 606/10 |
| 4,764,930 | 8/1988 | Bille et al. . |
| 4,773,414 | 9/1988 | L'Esperance, Jr. . |
| 4,784,135 | 11/1988 | Blum et al. . |
| 4,798,204 | 1/1989 | L'Esperance, Jr. . |
| 4,838,266 | 6/1989 | Koziol et al. . |
| 4,840,175 | 6/1989 | Peyman . |
| 4,848,340 | 7/1989 | Bille et al. . |
| 4,856,513 | 8/1989 | Muller . |
| 4,862,886 | 9/1989 | Clarke et al. . |
| 4,901,718 | 2/1990 | Bille et al. ................................ 606/4 |
| 4,903,695 | 2/1990 | Warner et al. . |
| 4,911,711 | 3/1990 | Telfair et al. . |
| 4,925,523 | 5/1990 | Braren et al. . |
| 4,941,093 | 7/1990 | Marshall et al. . |
| 4,975,918 | 12/1990 | Morton . |
| 4,994,058 | 2/1991 | Raven et al. . |
| 5,019,074 | 5/1991 | Muller . |
| 5,052,004 | 9/1991 | Gratze et al. . |
| 5,065,046 | 11/1991 | Guyer . |
| 5,074,859 | 12/1991 | Koziol . |
| 5,108,388 | 4/1992 | Trokel . |
| 5,108,412 | 4/1992 | Krumeich et al. . |
| 5,144,630 | 9/1992 | Lin . |
| 5,163,934 | 11/1992 | Munnerlyn . |
| 5,163,936 | 11/1992 | Black et al. . |
| 5,182,759 | 1/1993 | Anthon et al. . |
| 5,188,631 | 2/1993 | L'Esperance, Jr. . |
| 5,196,006 | 3/1993 | Klopotek et al. . |
| 5,207,668 | 5/1993 | L'Esperance, Jr. ..................... 606/10 |
| 5,217,452 | 6/1993 | O'Donnell . |
| 5,219,343 | 6/1993 | L'Esperance, Jr. ..................... 606/10 |
| 5,219,344 | 6/1993 | Yoder, Jr. . |
| 5,226,903 | 7/1993 | Mizuno . |
| 5,257,988 | 11/1993 | L'Esperance, Jr. . |
| 5,263,950 | 11/1993 | L'Esperance, Jr. . |
| 5,284,477 | 2/1994 | Hanna et al. . |
| 5,312,320 | 5/1994 | L'Esperance, Jr. . |
| 5,324,281 | 6/1994 | Muller . |
| 5,334,190 | 8/1994 | Seiler . |
| 5,336,217 | 8/1994 | Buys et al. ............................... 606/12 |
| 5,353,262 | 10/1994 | Yakymyshyn et al. . |
| 5,360,424 | 11/1994 | Klopotek . |
| 5,363,388 | 11/1994 | Shi et al. . |
| 5,364,388 | 11/1994 | Koziol . |
| 5,370,641 | 12/1994 | O'Donnell, Jr. . |
| 5,391,165 | 2/1995 | Fountain et al. ......................... 606/4 |
| 5,395,356 | 3/1995 | King et al. . |
| 5,395,362 | 3/1995 | Sacharoff et al. . |
| 5,405,355 | 4/1995 | Peyman et al. . |
| 5,411,501 | 5/1995 | Kloptek . |
| 5,423,801 | 6/1995 | Marshall et al. . |
| 5,425,727 | 6/1995 | Koziol . |
| 5,425,729 | 6/1995 | Ishida et al. . |
| 5,437,658 | 8/1995 | Muller et al. . |
| 5,442,487 | 8/1995 | Mizuno . |
| 5,445,633 | 8/1995 | Nakamura et al. . |
| 5,461,212 | 10/1995 | Seiler et al. . |
| 5,470,329 | 11/1995 | Sumiya . |
| 5,480,396 | 1/1996 | Simon et al. ............................. 606/4 |
| 5,505,723 | 4/1996 | Muller . |
| 5,507,741 | 4/1996 | L'Esperance, Jr. . |
| 5,507,799 | 4/1996 | Sumiya . |
| 5,520,679 | 5/1996 | Lin ............................................ 606/5 |
| 5,533,997 | 7/1996 | Ruiz .......................................... 606/5 |
| 5,549,597 | 8/1996 | Shimmick et al. . |
| 5,549,599 | 8/1996 | Sumiya ................................... 606/12 |
| 5,556,395 | 9/1996 | Shimmick et al. . |
| 5,599,340 | 2/1997 | Simon et al. ............................. 606/5 |
| 5,613,965 | 3/1997 | Muller . |
| 5,624,436 | 4/1997 | Nakamura et al. . |
| 5,634,919 | 6/1997 | Azar ........................................ 606/10 |
| 5,637,109 | 6/1997 | Sumiya . |
| 5,646,791 | 7/1997 | Glockler . |
| 5,651,784 | 7/1997 | Klopotek . |
| 5,683,379 | 11/1997 | Hohla ...................................... 606/10 |
| 5,711,762 | 1/1998 | Trokel . |
| 5,713,892 | 2/1998 | Shimmick . |
| 5,735,843 | 4/1998 | Trokel . |
| 5,849,006 | 12/1998 | Frey et al. ................................ 606/4 |
| 5,904,678 | 5/1999 | Pop ............................................ 606/4 |

OTHER PUBLICATIONS

J.T. Lin, J.L. Montgomery, "Temperature—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", KDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, Third—Harmonic Generation of an Alexandrite Laser in $\beta$–$BaB_2O_4$, Applied Physics Letters, May 1989, pp. 1206–1208.

Conference on Lasers and Electro–Optics, Optical Society of America, Apr. 1989, p. 390.

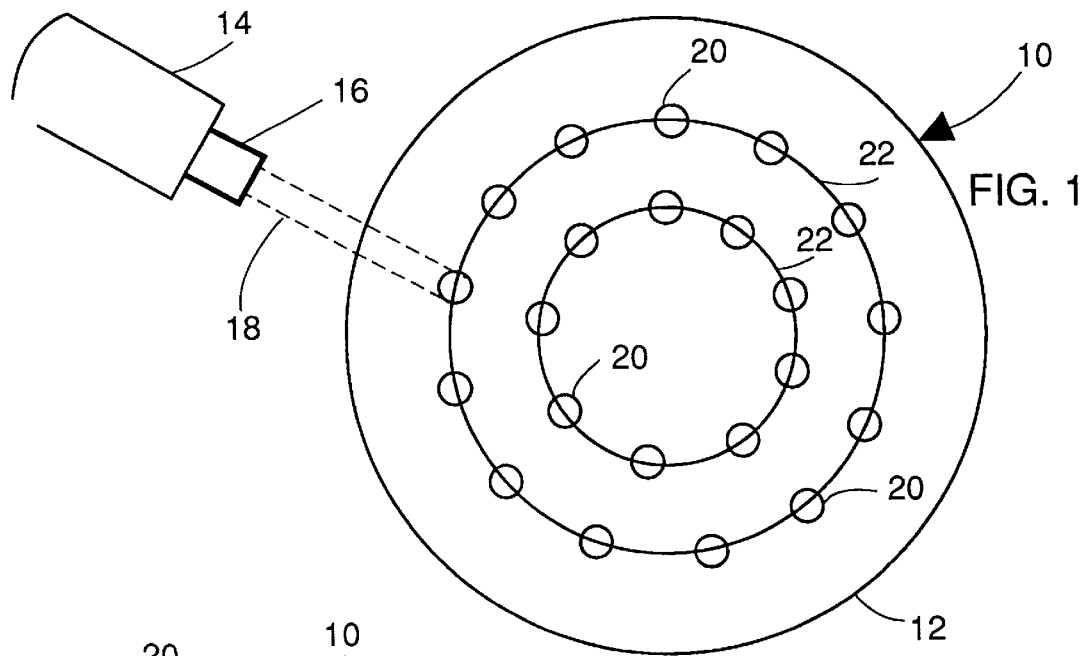
FIG. 1
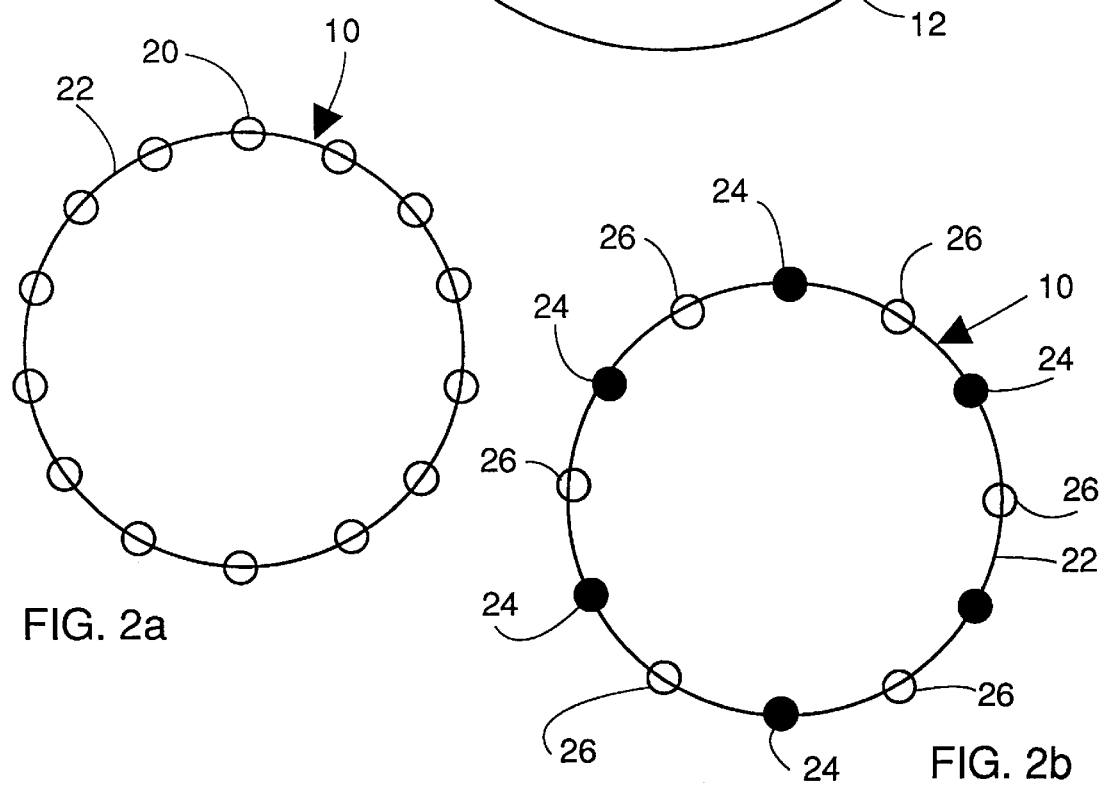
FIG. 2a
FIG. 2b

METHOD AND APPARATUS FOR CONTROLLING SCANNING OF AN ABLATING LASER BEAM

BACKGROUND OF THE INVENTION

1. Field of the Invention

This invention relates generally to a method and apparatus for ablating tissue, and more particularly, it relates to a method and apparatus for ablating tissue which results in a smooth reshaping of, e.g., a cornea of an eye, with an ablating laser beam by directing the laser beam to incremental ablation points or spots in a predetermined pattern on the tissue to be ablated.

2. Description of the Prior Art

The ablation of human tissue with an ablating laser beam is known. Typically, a laser beam is incrementally scanned across a layer of tissue to be ablated, and adjacent points or spots on the layer of tissue are sequentially ablated to reshape the tissue.

For example, laser ablation is utilized to reshape a cornea of an eye. The human eye functions much like a camera, with a lens in front and a light-sensitive screen, the retina, in the rear. Images enter the eye through the cornea which is a transparent domed window located at the front of the eye. In a normal-visioned eye, the cornea bends or refracts incoming images, causing the images to focus on the retina. The inability of the cornea to refract incoming images properly causes blurred vision and is called a refractive disorder. Myopia (near sightedness) is one of the most common refractive disorders. In a nearsighted eye, the cornea is too steep, causing an image to be focused in front of the retina, and distant objects to appear blurred.

To correct near sightedness, laser vision correction (Photorefractive Keratectomy or PRK) can be performed to make the cornea less steep by removing a microscopic layer of the cornea through a gentle reshaping technique. The laser produces an invisible beam of ultraviolet light which removes microscopic amounts of corneal tissue at adjacent points in a scan without causing damage to surrounding cells.

To achieve most corrections, a microscopic amount of corneal tissue approximately a third the thickness of a human hair—is sculpted from the surface of the cornea. The laser beam is directed onto the surface of the eye in a series of adjacent pulses along a linear path. Each pulse removes approximately one quarter of a micron of tissue (one hundred thousandths of an inch). The reshaping is successful by removing the layers of the cornea which cause distant objects to be focused more properly on the retina of the eye. The precision of a laser beam assures total control of the correction process with the integrity and the strength of the cornea being preserved.

Conventional laser ablation for vision correction has achieved good results, with the majority of patients no longer dependent on corrective lenses after the treatment. However, it is important to achieve a smooth ablation such that that remaining tissue does not contain any significant ridges or other rough areas. Accordingly, there exists a need for a method and apparatus for performing laser vision surgery which accurately and effectively ablates tissue such that a smooth surface remains. Improved apparatus and methods for achieving a smooth ablation, such as improved ablation patterns, are needed.

SUMMARY OF THE INVENTION

In accordance with the principles of the present invention, a method and apparatus for ablating tissue with an ablating laser beam is provided. A first scan line is defined in an ablation zone on the tissue to be ablated. A plurality of laser beam ablation points along the first scan line are defined, either explicitly or implicitly by subsequent ablation. At least two passes along the first scan line are performed to ablate the laser beam ablation points.

In another aspect of the present invention two or more passes along the scan line are performed, and only non-adjacent laser beam ablation points along the first scan line are ablated during each pass. The two or more passes along the one scan line result in a single ablation of each laser beam ablation point.

BRIEF DESCRIPTION OF THE DRAWINGS

Features and advantages of the present invention will become apparent to those skilled in the art from the following description with reference to the drawings, in which:

FIG. 1 is a top plan view illustrating a circular or elliptical scanning technique of the method and apparatus for performing laser ablation in accordance with the principles of the present invention;

FIG. 2a is a top view illustrating a sequential ablation of ablation points in a circular or elliptical scanning technique in accordance with the principles of the present invention;

FIG. 2b is a top view illustrating an alternative sequence of ablation of the ablation points in the circular or elliptical scanning technique in accordance with the principles of the present invention;

DETAILED DESCRIPTION OF THE ILLUSTRATIVE EMBODIMENTS

Figure 3A:
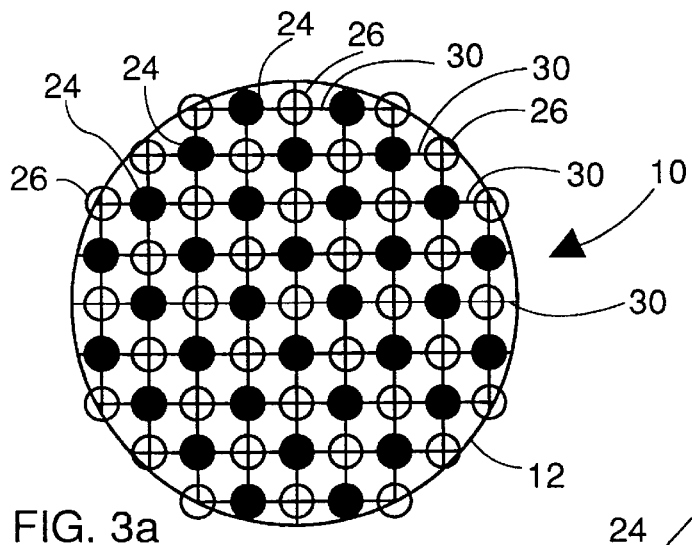
FIG. 3a is a top plan view illustrating a circular ablation zone with an intermittent linear scan technique of the method and apparatus for performing laser ablation in accordance with the principles of the present invention.

As illustrated in FIG. 1, the present invention is a method and apparatus for performing laser ablation to remove or reshape human tissue, e.g., corneal tissue in a cornea 10 of an eye 12. Although the embodiments of the present invention are described with reference to the removal of corneal tissue, the present invention relates to laser ablation techniques of human tissue in general. Moreover, with respect to the application of the present invention for the reshaping of a cornea, the method and apparatus of the present invention further relates to use in laser refractive keratectomy (e.g. photorefractive keratectomy or PRK, PRK after radial keratomy, laser keratectomy with mircrokeratome, intrastromal photodisruption), laser therapeutic keratectomy, and laser lamellar resection.

Basically, when more laser energy is deposited on the desired position on the tissue to be ablated, more tissue is removed and when less energy is deposited on the desired position on the tissue, less tissue is removed. A layer of the tissue is removed by ablating specific ablation points or spots in a predetermined ablation zone of the tissue.

The actual distance between each of the ablation points or spots is determined such that the amount of ablation yields a substantially smooth cornea surface. Other factors to be considered include the fume from the ablation, the wetness of the tissue surface, and the difference of absorption on different positions of the tissue surface.

FIG. 1 shows a laser beam delivery system 14 having a laser head 16. The laser beam delivery system 14 generates a pulsed ablating laser beam 18 and includes a combination of optical elements that attenuate, shape, direct and otherwise control the ablating laser beam 18 to the various ablation points or spots in an ablation zone predetermined on tissue to be ablated, e.g., a cornea 12 to be treated.

The diameter of the laser beam spot 20 of the laser beam 18 on the cornea 12 is controllable to vary in the range from approximately 0.1 millimeter to approximately 1 millimeter and is scanned on the cornea 12 by a scanner in the beam delivery system 14. The scanner includes at least one mirror driven by at least one computer-controlled galvanometer.

The thickness of the tissue to be ablated is divided into a number of layers, each layer typically being ablated individually. The number of layers of tissue to be ablated at the various positions depends on the thickness of the tissue to be removed. In operation, the laser beam 18 is directed toward the tissue to be ablated, and the laser beam delivery system 14 is intermittently activated to produce a predetermined amount of laser energy to ablate predetermined intermittent ones of the ablation points or spots in a linear scan. The term "intermittent" herein refers to non-adjacent ablation points or spots along a single scan or pass through the ablation zone.

The method and apparatus of the present invention, when applied to vision correction, provides several techniques to achieve smoother ablation than is currently known. The method and apparatus of the present invention scans a laser beam 18 across an ablation zone on a cornea 12 of an eye in a predetermined scan pattern selected in accordance with the desired ablation rate. However, rather than ablating tissue at each subsequent ablation point along each scan line of the predetermined pattern, the present invention provides for multiple passes along the scan line and intermittent ablation of the ablation points along the scan lines during each pass of the laser beam 18 through the ablation zone. In accordance with the principles of the present invention, subsequent pass(es) along the same scan line are later performed to cause ablation at non-adjacent ablation points between those points already ablated in a previous linear pass through the ablation zone.

The intermittent nature of the ablation, i.e., ablating every other, every third, every fourth, etc. ablation point in any one pass through the ablation zone results in a smooth tissue surface remaining after the ablation procedure. Thus, in the case of reshaping the cornea 12 of an eye, the apparatus and method results in a smoother reshaping.

The intermittent ablation of the present invention is described in four embodiments, although intermittent ablation and multiple passes along a same scan line have uses beyond the uses as described.

(1) Circular or Elliptical Intermittent Ablation

As illustrated in FIG. 1, the method of the present invention includes scanning circular or elliptical patterns on the cornea 12. The circular or elliptical pattern consists of concentric circular or elliptic scan lines 22 with progressive, either increasing or decreasing, radii. The distance between the laser beam ablation points or spots 20, both in the radial and the tangential directions, are generally adjustable to yield smoothness and uniformity of the corneal surface.

To yield an even smoother surface, the laser beam ablation points or spots 20 can be intermittently ablated along each scan line 22. FIGS. 2a and 2b show examples of the scanning and ablating sequence for each scan line 22.

FIG. 2a depicts a sequential ablation of each laser beam ablation point or spot 20 on along the scan line 22. The scan may start at any point along the circular scan line 22, and continue around 360 degrees in a single pass until all laser beam ablation points 20 are ablated.

FIG. 2b depicts an intermittent ablation of the laser beam ablation points 24, 26 along each circular scan line 22. The scan may start at any point along the circular scan line 22, and continue around in a first pass for 360 degrees, ablating every other laser beam ablation point 24. Thereafter, either immediately after the first pass of the circular scan line 22, or after subsequent scans of other scan lines occurs, a second pass is made on the circular scan line 22 to ablate the unablated laser beam ablation points 26 which were not ablated during the first pass. This subsequent pass on the same circular scan line 22 performs ablation of every other (or every third, every fourth, etc.) laser beam ablation point 26, resulting in the complete ablation of all laser beam ablation points 24, 26 along the circular scan line 22. The filled dots 24 represent the laser beam ablation points or spots 20 that are ablated during the first pass of the circular scan line 22, and the hollow dots 26 represent the laser beam ablation points or spots 20 that are scanned during a second or subsequent pass of the circular scan line 22.

It should be noted that it is within the scope of the present invention to ablate all the laser beam ablation points denoted by filled dots 24 on different circular scan lines 22 on the same (or different) layer of the tissue first, and subsequently ablate the laser beam ablation points denoted by the hollow dots 26 on the same scan line 22.

Moreover, it is to be noted that although FIG. 2b depicts ablating every other laser beam ablation point during each pass along a scan line, it is also within the present invention to ablate every third, every fourth, every fifth, etc. laser beam spot 20, and repeating the scanning cycle until all laser beam ablation points on each scan line 22 are ablated.

It also follows that the present invention can be employed in elliptical pattern scan lines, polygonal pattern scan lines, or any other ablation pattern containing concentric scan lines.

(2) Linear Intermittent Ablation

Figure 3B:
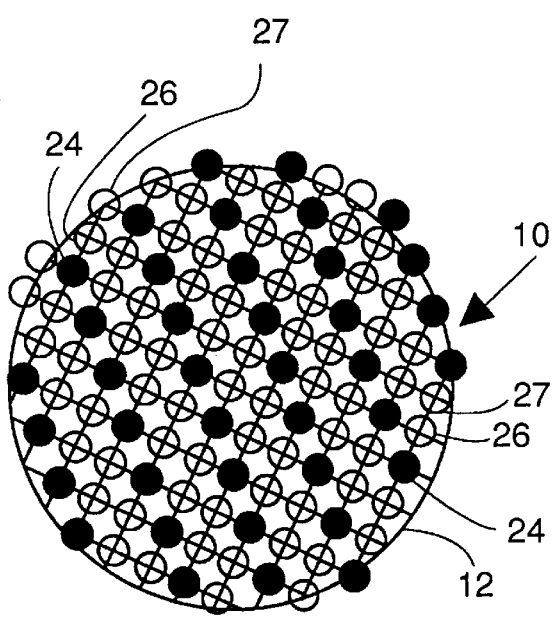
FIG. 3b is a top plan view illustrating a circular ablation zone with an alternative intermittent ablation sequence of the linear scan technique as illustrated in FIG. 3a in accordance with the principles of the present invention.

A second technique of the present invention which provides a smooth ablation is referred to herein as a linear intermittent ablation. As illustrated in FIGS. 3a and 3b, this embodiment comprises straight scan lines 30 across an ablation zone 10, and intermittent ablation of laser beam ablation points 24, 26, 27 on each straight scan line 30. FIG. 3a shows ablation of every other laser beam ablation point 24, 26, and FIG. 3b shows ablation of every third laser beam ablation point 24, 26, 27.

In particular, FIG. 3a illustrates an example of a circular ablation zone with a predetermined pattern of straight linear scan lines of laser beam ablation points 25 24, 26. At the completion of the ablation procedure, all laser beam ablation points 24, 26 will have been ablated. However, in accordance with the present invention, the sequence of ablation has been found to be related to the resulting smoothness of the ablated tissue. Thus, the laser beam ablation points 24, 26 are not ablated sequentially along each scan line 30. Instead, the sequence is varied in a fashion similar to that described with respect to Circular or Elliptical Intermittent Ablation herein above. For example, every third, every fourth, every fifth, etc. laser beam ablation point may be ablated during any one pass of each straight scan line 30. Moreover, passes on other straight scan lines 30 may occur between subsequent passes on any one straight scan line 30. Thus, intermediate laser beam ablation points or spots between the originally ablated laser beam ablation points or spots 20 can be ablated, e.g., after the entire tissue layer is scanned, or immediately after the first pass of the straight scan line 30 is performed.

The orientation of the resulting "lattice" between laser beam ablation points 24, 26, 27 for subsequent tissue layers can be varied or rotated between layers as desired to provide increased smoothness of the resulting tissue surface. For example, FIG. 3b illustrates movement of the "lattice" with respect to the positioning of FIG. 3A. Moreover, the "lattice" orientation angle can be adjusted for optimum result. Thus, it is possible to ablate layers with scan lines along different orientations with respect to subsequently ablated tissue layers.

(3) Proportionally Randomized Scan

The method and apparatus of the present invention further includes a technique of establishing a randomized pattern across an ablation zone, but containing an ablation density which is kept substantially constant across any one layer of tissue to be removed.

In any predetermined layer of an ablation zone, the laser beam ablation points or spots 20 are disbursed about the ablation zone in a randomized manner, but the total number of ablated ablation points or spots is limited to a desired ratio with respect to the area of the ablation zone and based on the desired thickness of the layer to be removed.

Accordingly, the laser beam ablation points or spots in each layer of the tissue to be removed are not aligned in a regular array as in the circular or elliptical scan technique, or as in the linear scan technique, but instead are distributed in a randomized manner. The result is that the ablating sequence of the ablation points is naturally randomized and made intermittent.

The average thickness of each tissue layer is maintained relatively constant by ablating in each tissue layer only a number of laser beam ablation points or spots 20 preferably proportional to the area of the tissue layer being removed from the ablation zone.

(4) Annularly Zonal Ablation

Figure 4:
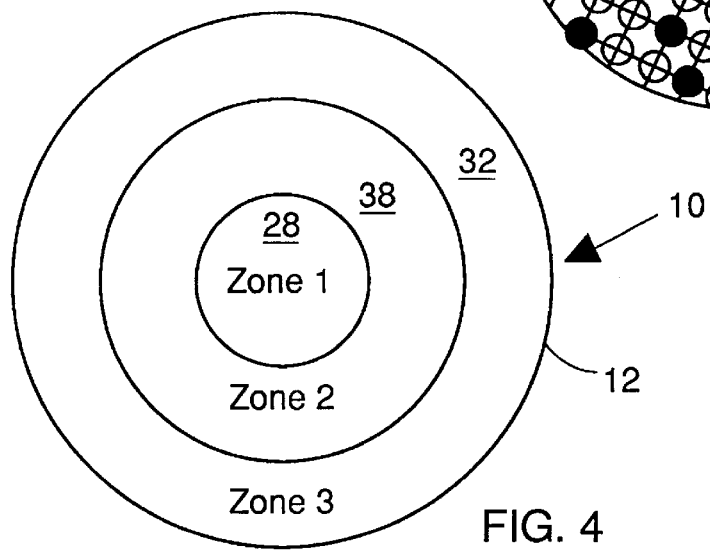
FIG. 4 is a top plan view illustrating annular ablation in accordance with the principles of the present invention.

As illustrated in FIG. 4, according to another embodiment of the present invention, the substantially whole thickness of all tissue layers of the ablation zone is divided into annular zones ZONE 1, ZONE 2, ZONE 3. Of course, it is to be understood by those of skill in the art that any desired annular patterns can be formed into annular zones in accordance with the principles of this embodiment of the present invention.

In the shown example, a circularly symmetrical ablation pattern is predetermined for a treatment area of the cornea 12 of an eye. The substantially whole treatment area is divided into a number of annular zones 28, 38, 32. The specific number of annular zones 28, 38, 32 are empirically chosen to result in optimum smoothness and accuracy of the resulting ablated surface of the cornea 12. The intermittent techniques described herein above, including the proportionally randomized scan, may be applied to the annular zones 28, 38, 32 in accordance with this aspect of the present invention to result in a smooth ablated tissue surface.

In all embodiments, the laser beam ablation points or spots represent the center point of an ablating laser beam on the surface of the tissue to be ablated. However, those of ordinary skill in the art will appreciate that the energy of the laser beam typically extends beyond the bounds of the depicted laser beam ablation points or spots causing areas of ablated tissue to overlap. The overlapping of the ablated tissue and/or the number of laser beam ablation points or spots in the ablation zone is empirically determined to yield optimum results, i.e., surface smoothness, accuracy of reshaping, etc.

It is of course within the scope of the present invention to have the boundary of the scan patterns, i.e., the ablation zone, be circular, elliptical, annular, rectangular, polygonal, or any other shape, as desired.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only by the appended claims. Moreover, the invention as disclosed herein may be suitably practiced in the absence of specific elements which are disclosed herein.

We claim:

1. A method of ablating tissue with an ablating laser beam, said method comprising:

defining a first scan line in an ablation zone on said tissue;
    defining a plurality of laser beam ablation points along said first scan line; and performing at least two passes along said first scan line to ablate said tissue at each of said plurality of laser beam ablation points;

wherein during each of said at least two passes along said first scan line, substantially only non-adjacent ones of said plurality of laser beam ablation points are ablated along said first scan line.

2. The method of ablating tissue according to claim 1, wherein:

said step of performing at least two passes along said first scan line accomplishes a single ablation at each of said plurality of laser beam ablation points.

3. The method of ablating tissue according to claim 1, wherein during each of said at least two passes along said first scan line, ablation is performed at no fewer than every other laser beam ablation point.

4. The method of ablating tissue according to claim 1, wherein:

said ablated tissue is corneal tissue.

5. The method of ablating tissue according to claim 1, wherein:

said first scan line is a circular scan line.

6. The method of ablating tissue according to claim 1, wherein:

said first scan line is a straight linear scan line.

7. The method of ablating tissue according to claim 6, wherein:

said first scan line is angled with respect to a straight linear scan line on a previously ablated layer of said tissue.

8. The method of ablating tissue according to claim 1, wherein:

at least three passes are made along said first scan line to accomplish a single ablation at each of said plurality of laser beam ablation points.

9. The method of ablating tissue according to claim 8, wherein:

during each of said at least three passes, ablation is performed at no fewer than every third laser beam ablation point.

10. The method of ablating tissue according to claim 1, wherein:

at least four passes are made along said first scan line to accomplish a single ablation at each of said plurality of laser beam ablation points.

11. The method of ablating tissue according to claim 10, wherein:

during each of said at least four passes, ablation is performed at no fewer than every fourth laser beam ablation point.

12. The method of ablating tissue according to claim 1, further comprising:

defining a plurality of scan lines in said ablation zone including said first scan line;

defining a plurality of laser beam ablation points along each of said plurality of scan lines; and wherein said step of performing at least two passes comprises:

performing a first pass along each of said plurality of scan lines, said first pass comprising ablating tissue at substantially only non-adjacent ones of said plurality of laser beam ablation points along each of said plurality of scan lines, and performing a subsequent pass along each of said plurality of scan lines, said subsequent pass resulting in ablation at substantially all of said plurality of laser beam ablation points along each of said plurality of scan lines.

13. A method of ablating tissue with an ablating laser beam, said method comprising:

defining a first scan line in an ablation zone on said tissue;

defining a plurality of laser beam ablation points along said first scan line;

performing a first pass along said first scan line, said first pass comprising ablating tissue at substantially only non-adjacent ones of said plurality of laser beam ablation points along said first scan line; and performing a subsequent pass along said first scan line, said subsequent pass resulting in ablation at substantially all of said plurality of laser beam ablation points along said first scan line.

14. The method of ablating tissue according to claim 13, wherein:

said step of performing said first pass and said step of performing said subsequent pass together accomplish a single ablation of each of said plurality of laser beam ablation points.

15. The method of ablating tissue according to claim 13, wherein:

said ablated tissue is corneal tissue.

16. The method of ablating tissue according to claim 13, wherein:

said first scan line is a circular scan line.

17. The method of ablating tissue according to claim 13, wherein:

said first scan line is a straight linear scan line.

18. The method of ablating tissue according to claim 17, wherein:

said first scan line is angled with respect to a straight linear scan line on a previously ablated layer of said tissue.

19. The method of ablating tissue according to claim 13, wherein:

at least three passes are made along said first scan line to accomplish a single ablation at said substantially all of said plurality of laser beam ablation points along said first scan line.

20. The method of ablating tissue according to claim 19, wherein:

during each of said at least three passes, ablation is performed at no fewer than every third laser beam ablation point.

21. The method of ablating tissue according to claim 13, wherein:

at least four passes are made along said first scan line to accomplish a single ablation at each of said plurality of laser beam ablation points.

22. The method of ablating tissue according to claim 21, wherein:

during each of said at least four passes, ablation is performed at no fewer than every fourth laser beam ablation point.

23. The method of ablating tissue according to claim 13, further comprising:

defining a plurality of scan lines in said ablation zone including said first scan line;

defining a plurality of laser beam ablation points along each of said plurality of scan lines;

performing a first pass along each of said plurality of scan lines, said first pass comprising ablation at substantially only non-adjacent ones of said plurality of laser beam ablation points along each of said plurality of scan lines; and performing a subsequent pass along each of said plurality of scan lines, said subsequent pass resulting in ablation at substantially all of said plurality of laser beam ablation points along each of said plurality of scan lines.

24. A method for reshaping a cornea of an eye with a laser beam delivery system, said method comprising:

producing a laser beam with said laser beam delivery system;

directing said laser beam to incremental laser beam ablation points on said cornea in a predetermined line scan pattern;

ablating said cornea at non-adjacent ones of each of said incremental laser beam ablation points during each pass of at least two passes along said predetermined line scan pattern with said laser beam; and incrementally varying a radius of said predetermined line scan pattern until a desired reshaping of said cornea is achieved.

25. The method according to claim 24, further comprising:

directing said laser beam on said cornea in a generally circular pattern.

26. The method according to claim 24, further comprising:

directing said laser beam on said cornea in a generally elliptical pattern.

27. The method according to claim 24, further comprising:

directing said laser beam in a generally annular line scan pattern based on a group consisting of a circular, elliptical, annular, and rectangular predetermined line scan pattern.

28. The method according to claim 24, further comprising:

directing said laser beam on said cornea in a generally randomized pattern within a predetermined annular ablation zone.

29. The method according to claim 24, wherein:

said incrementally varying said radius of said predetermined line scan pattern incrementally increases said radius.

30. The method according to claim 24, wherein:

said incrementally varying said radius of said predetermined line scan pattern incrementally decreases said radius.

31. Apparatus for controlling scanning of an ablating laser beam, said apparatus comprising:

means for defining a first scan line in an ablation zone on said tissue;

means for defining a plurality of laser beam ablation points along said first scan line; and means for performing at least two passes along said first scan line to ablate said tissue at each of said plurality of laser beam ablation points;

wherein during each of said at least two passes along said first scan line, substantially only non-adjacent ones of said plurality of laser beam ablation points are ablated along said first scan line.

32. Apparatus for controlling scanning of an ablating laser beam according to claim 31, wherein:

said means for performing at least two passes along said first scan line accomplishes a single ablation at each of said plurality of laser beam ablation points.

33. Apparatus for controlling scanning of an ablating laser beam, said apparatus comprising:

means for defining a first scan line in an ablation zone on said tissue;

means for defining a plurality of laser beam ablation points along said first scan line;

means for performing a first pass along said first scan line, said first pass comprising ablating tissue at substantially only non-adjacent ones of said plurality of laser beam ablation points along said first scan line; and means for performing a subsequent pass along said first scan line, said subsequent pass resulting in ablation at substantially all of said plurality of laser beam ablation points along said first scan line.

34. The apparatus for controlling scanning of an ablating laser beam according to claim 33, wherein:

said means for performing a first pass and said means for performing said subsequent pass together accomplish a single ablation of each of said plurality of laser beam ablation points.

* * * * *